United States Patent
Nardi

(10) Patent No.: US 9,161,825 B2
(45) Date of Patent: Oct. 20, 2015

(54) COUPLING ASSEMBLY, PARTICULARLY FOR DENTAL IMPLANTS

(75) Inventor: Ezio Nardi, Bologna (IT)

(73) Assignee: OT IMPLANT S.R.L., Bologna (IT)

( * ) Notice: Subject to any disclaimer, the term of this patent is extended or adjusted under 35 U.S.C. 154(b) by 191 days.

(21) Appl. No.: 12/662,837

(22) Filed: May 6, 2010

(65) Prior Publication Data

US 2010/0285426 A1 Nov. 11, 2010

(30) Foreign Application Priority Data

May 7, 2009 (IT) .............................. BO2009A0279

(51) Int. Cl.
*A61C 13/225* (2006.01)
*A61C 8/00* (2006.01)
*A61C 13/265* (2006.01)

(52) U.S. Cl.
CPC ............. *A61C 8/0048* (2013.01); *A61C 8/0001* (2013.01); *A61C 13/2656* (2013.01)

(58) Field of Classification Search
CPC .... A61C 8/0048; A61C 8/005; A61C 8/0051; A61C 8/0053; A61C 8/0054; A61C 8/0056; A61C 8/0057; A61C 8/0059; A61C 8/0062; A61C 8/0063; A61C 8/0066; A61C 8/0069; A61C 8/0075; A61C 8/00; A61C 8/77; A61C 8/0092; A61C 8/0093
USPC ........... 433/167–168.1, 172–176, 201.1, 181; 606/301–321
See application file for complete search history.

(56) References Cited

U.S. PATENT DOCUMENTS

| | | | | |
|---|---|---|---|---|
| 3,514,858 A | * | 6/1970 | Silverman | 433/174 |
| 4,290,755 A | * | 9/1981 | Scott | 433/173 |
| 4,631,031 A | * | 12/1986 | Richter | 433/173 |
| 4,722,688 A | * | 2/1988 | Lonca | 433/173 |
| 4,907,969 A | * | 3/1990 | Ward | 433/173 |
| 4,938,694 A | * | 7/1990 | Ledermann | 433/173 |
| 5,211,561 A | * | 5/1993 | Graub | 433/169 |
| 5,417,570 A | * | 5/1995 | Zuest et al. | 433/177 |
| 6,030,219 A | | 2/2000 | Zuest et al. | |
| 6,716,030 B1 | * | 4/2004 | Bulard et al. | 433/174 |
| 2004/0005530 A1 | * | 1/2004 | Mullaly et al. | 433/172 |
| 2006/0111715 A1 | * | 5/2006 | Jackson | 606/61 |
| 2008/0114404 A1 | * | 5/2008 | Matthis et al. | 606/309 |
| 2008/0153063 A1 | | 6/2008 | Mullaly et al. | |
| 2008/0261174 A1 | | 10/2008 | Gittleman | |
| 2010/0203476 A1 | * | 8/2010 | Studer et al. | 433/173 |

FOREIGN PATENT DOCUMENTS

RU 1836059 A3 8/1993

* cited by examiner

*Primary Examiner* — Yogesh Patel
(74) *Attorney, Agent, or Firm* — Modiano & Associati; Albert Josif; Daniel J. O'Byrne

(57) ABSTRACT

A coupling assembly, particularly for dental implants, having at least one pin, which can be coupled rigidly to a bone portion, and a supporting element, which can be associated with a prosthesis. The pin has, at its end portion that lies opposite the one designed for connection to the bone portion, a protruding tab that can be accommodated by elastic forcing in a respective cavity formed in the supporting element so as to produce a stable coupling configuration between the pin and the supporting element. The tab is shaped like a substantially equatorial portion of a sphere with an outer lateral surface adapted to abut, with at least one part thereof, against the internal side wall of the cavity, to determine stable coupling configuration.

14 Claims, 6 Drawing Sheets

COUPLING ASSEMBLY, PARTICULARLY FOR DENTAL IMPLANTS

BACKGROUND OF THE INVENTION

As is known, one of the most effective solutions to the problem of loss of one or more teeth is to resort to a dental implant (provided in the ways that will be described hereinafter).

A larger number of these implants can of course be used to replace a plurality of missing teeth; as an alternative, faced with the lack of several teeth, the patient can receive a new dental arch, or a movable prosthesis which is provided monolithically, to be fixed to a plurality of implants.

According to one possible embodiment, a dental implant comprises an elongated pin, which is to be inserted in the upper or lower maxillary bone (in the position of the missing tooth) and substantially replicates the root of the lost tooth.

Externally to the gum, a supporting element protrudes from the pin and is designed to receive a retention cap which is associated with the prosthetic crown that simulates the original tooth.

In greater detail, the supporting element is substantially constituted by a spherical body: by applying a slight pressure it is possible to elastically accommodate such spherical body within a recess formed in the cap, thus achieving the desired coupling.

It is possible to resort to this type of coupling both to apply a single implant, designed to replace a missing tooth, and to apply a plurality of implants, which support a larger number of prosthetic crowns or a prosthesis that simulates an entire dental arch.

However, this solution is not free from drawbacks.

The sphere that protrudes from the gum in fact has a very substantial bulk, whereas the space within the mouth is minimal (especially if the mouth is to accommodate a prosthesis of the type of a dental arch).

Further, once the prosthesis has been disassembled (for cleaning, for example), one or more significantly protruding elements remain along the gum and cause discomfort when they come into contact with the antagonist part. In particular, the problem is especially felt when one does not wish to proceed immediately with reinsertion (for example to rest during the night).

Finally, it should be noted that during the operation for the application of a plurality of implants to a patient the surgeon often encounters difficulties in mutually aligning them precisely (for example due to a lack of parallelism of the pins inserted in the gum). Any displacements with respect to correct positioning allow insertion of the prosthesis only by forcing the coupling, with obvious traumas to the implants, which can compromise the correct outcome of the operation, with consequences that can even be as severe as premature loss of the pins or of the entire implant.

SUMMARY OF THE INVENTION

The aim of the present invention is to solve the above mentioned drawbacks, by providing a coupling assembly that makes it possible to contain the space occupation within the mouth, thus saving the patient an annoying discomfort.

Within this aim, an object of the invention is to provide a coupling assembly that can be used both for operations aimed at replacing one or more teeth and for operations aimed at installing a new dental arch.

Another object of the invention is to provide an assembly whose application during surgery ensures simply and effectively a correct positioning of the various components in order to jointly connect them to each other.

A further object of the invention is to propose a method that makes it possible to install a prosthesis in extremely short time and with a limited number of sessions at the dentist.

Another object of the invention is to provide an assembly that ensures high reliability in operation.

Another object of the invention is to provide an assembly that can be obtained easily starting from commonly commercially available elements and materials.

Another object of the invention is to provide an assembly that has low costs and is safe in application.

This aim and these and other objects which will become better apparent hereinafter are achieved by a coupling assembly, particularly for dental implants, which comprises at least one pin, that can be coupled rigidly to a bone portion and the like, and a supporting element, which can be associated with a prosthesis, said pin having, at its end portion that lies opposite the one designed for connection to the bone portion, a protruding tab which can be accommodated by elastic forcing in a respective cavity formed in said supporting element so as to produce a stable coupling configuration between said pin and said supporting element, characterized in that said tab is shaped like a substantially equatorial portion of a sphere, whose outer lateral surface is suitable to abut, with at least one of its parts, against the internal side wall of said cavity, to determine said stable coupling configuration.

BRIEF DESCRIPTION OF THE DRAWINGS

Further characteristics and advantages of the invention will become better apparent from the following detailed description of some preferred but not exclusive embodiments of the assembly according to the invention, illustrated by way of non-limiting example in the accompanying drawings, wherein:

FIG. 2 is a partially sectional front elevation view of the coupling assembly according to the invention;

FIG. 3 is an exploded perspective view of some components of the coupling assembly according to the invention;

FIG. 4 is a partially sectional front elevation view of the coupling assembly according to the invention;

FIG. 5 is a sectional front elevation view, taken along an axial plane, of a component of the coupling assembly according to the invention;

FIG. 6 is a top view of the component of FIG. 5;

DESCRIPTION OF THE PREFERRED EMBODIMENTS

Figure 1:
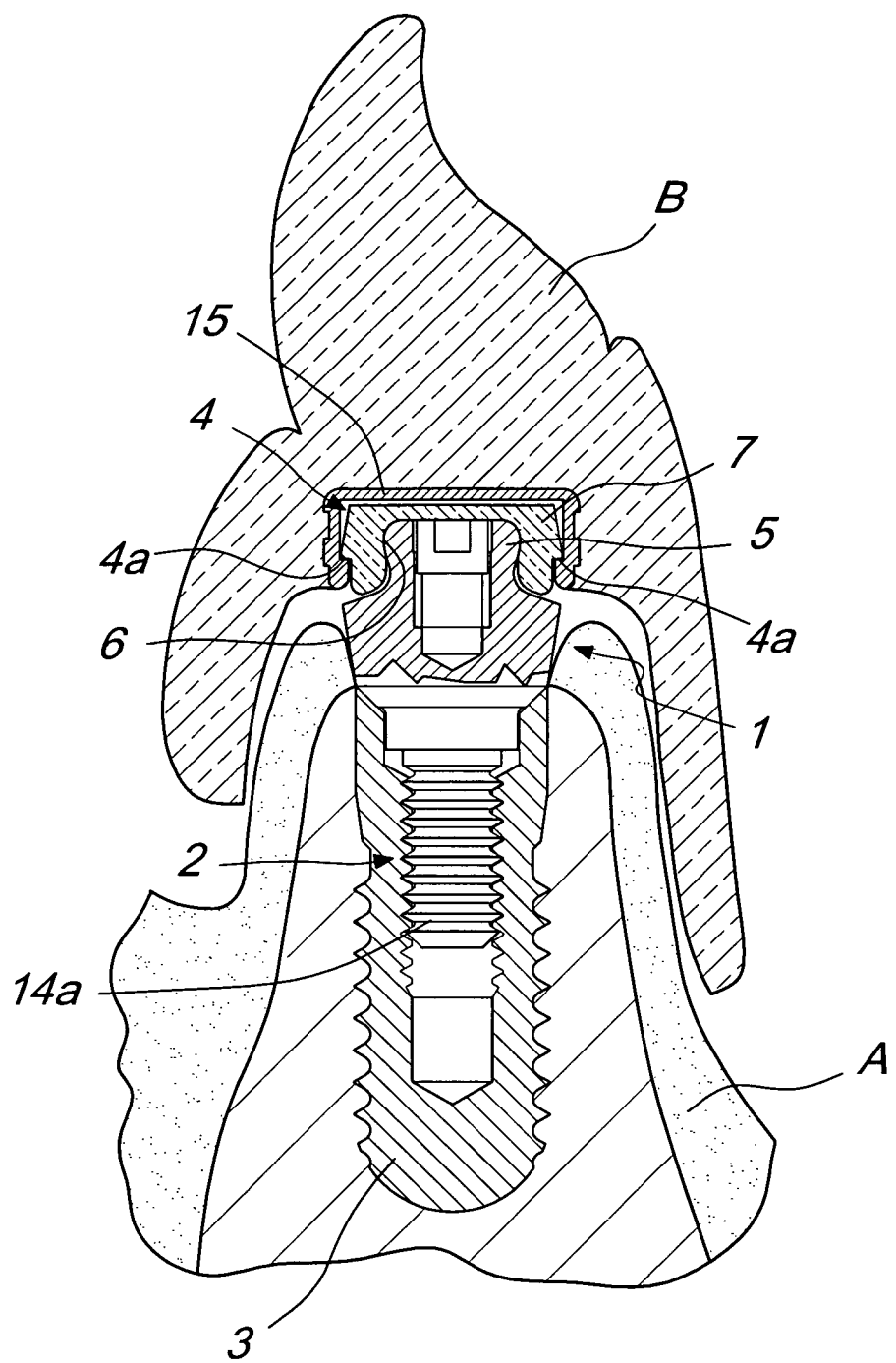
FIG. 1 is a partially sectional front elevation view of a coupling assembly according to the invention, in a first embodiment.

With reference to the figures, a coupling assembly according to the invention, generally designated by the reference numeral 1, comprises at least one pin 2, which can be coupled rigidly to a bone portion A and the like.

It should be noted from the outset that the bone portion A can be any part for which the application of the coupling assembly 1 according to the invention is suitable.

In the continuation of the present description, reference shall be made in any case to the preferred but not exclusive application in which the bone portion A is constituted by the upper or lower maxillary bone of a patient who, as a consequence of traumas or disorders of various kinds, requires the application of a prosthesis B, such as for example a simple dental crown, dentures or a dental bridge, to replace one or more missing teeth. According to this preferred application, the pin 2 is therefore substantially a dental implant.

It is specified that the pin 2 can be inserted directly in the bone portion A (as in the embodiment shown in FIG. 2); moreover, as can be seen in FIG. 1, it is possible to insert the pin 2 of the assembly 1 according to the invention in a preimplant 3, which is designed to mate stably with the surrounding anatomical tissues. The preimplant 3 can have a seat for the pin 2 inside it and can originate from a previous operation of the dentist.

The coupling assembly 1 according to the invention furthermore comprises a supporting element 4, which can be associated with or connected to the prosthesis B: the pin 2 has, at its first end portion that is opposite the second one designed for connection to the bone portion A, a protruding tab 5, which can be accommodated by elastic forcing in a respective cavity 6 formed in the supporting element 4.

Figure 2:
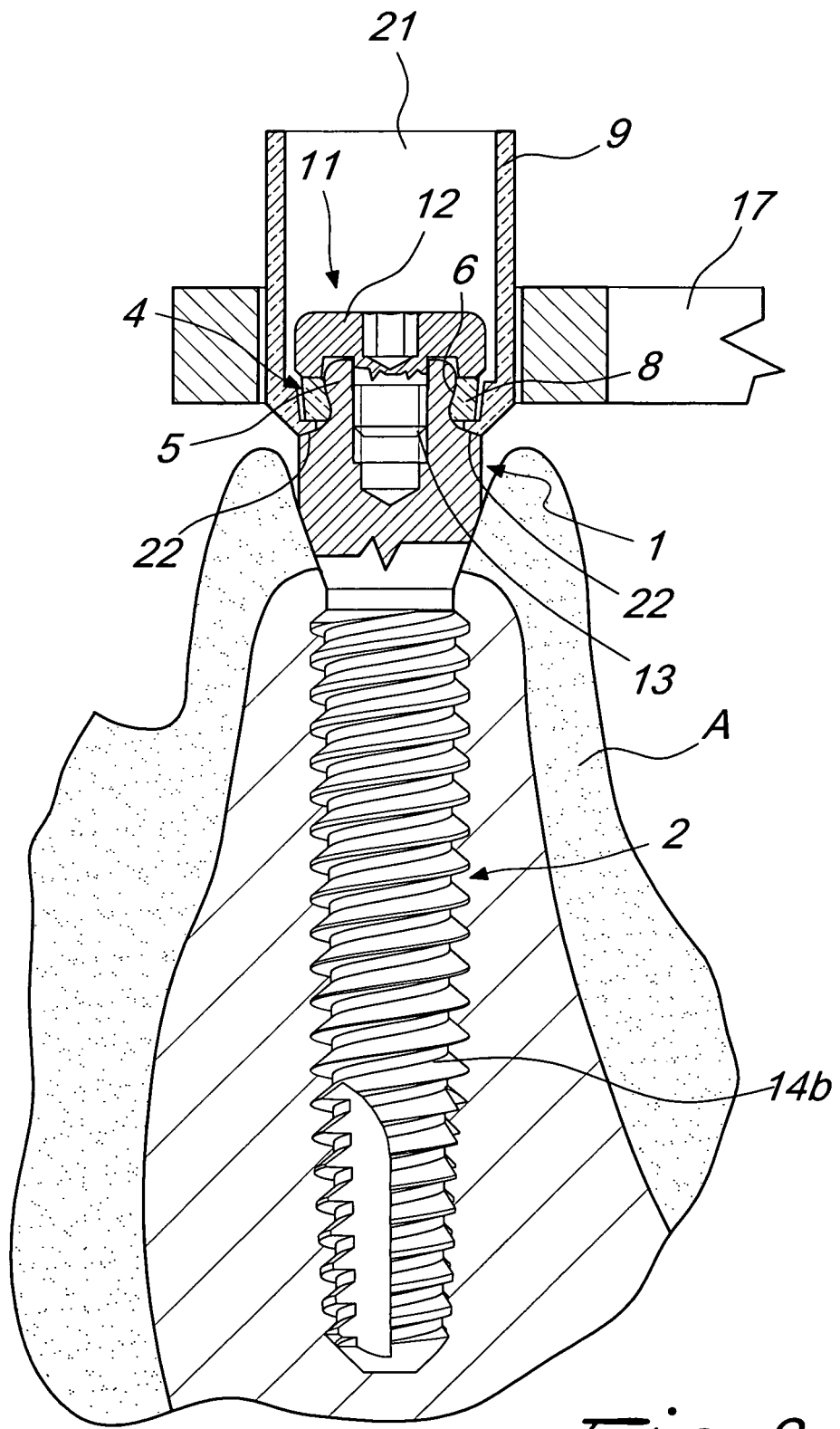
FIGS. 2 and 3 are views of the coupling assembly according to the invention in a second embodiment, and more particularly.

The accommodation of the tab 5 in the cavity 6 produces a stable coupling configuration between the pin 2 and the supporting element 4 (as shown in FIGS. 1 and 2), so as to make it possible to couple, in various ways, the prosthesis B to the bone portion A of the patient.

According to the invention, the tab 5 is shaped like a substantially equatorial portion of a sphere and its outer lateral surface is so shaped that is adapted to abut, with at least part thereof, on the inner side wall of the cavity 6 to produce the stable coupling configuration.

This specific shape of the coupling portion of the tab 5 can be obtained by intersecting (on opposite sides with respect to the center) a sphere with two planes which are parallel to each other and to a great circle of the sphere.

The resulting solid, having a disc shape, thus has two opposite end faces (at the intersection with the planes) and a lateral surface that in practice constitutes a fragment of the original spherical surface.

The choice to provide a tab 5 that is shaped according to the conditions described above ensures achievement of the intended aim and objects, since the reduced axial extension that they provide makes it possible to contain the space occupation of the assembly 1 within the mouth, without thereby compromising the correct and stable coupling between the pin 2 and the supporting element 4.

Other than in known assemblies, the outer lateral surface (which ensures the coupling by elastic forcing and/or interference by way of its curvature) in fact can be affected over its entirety by contact with the inner side walls of the cavity 6, thus ensuring the tightness of the coupling.

In practice, the tab 5 affected by the coupling is dimensionally similar to the portions of the tabs of known assemblies, in which only the equatorial region of the sphere that protrudes from the pin abutted against the supporting element.

The different shape assumed thus allows elimination of the portions that are unnecessary for coupling purposes and therefore to keep the stability of such coupling unchanged, with a reduced space occupation.

Further, it should be noted that in the coupling described and illustrated in the accompanying figures the reduced extension of the tab 5 in the mouth makes it possible to contain the extent of any flexural stresses discharged onto the bone portion A.

As a consequence for example of imperfect sizing of the various parts or of imperfect alignment of the pin 2, such stresses can in fact reach substantial values in known assemblies, because the spherical tab extends to a significant extent within the mouth, thus producing a considerable lever arm.

Moreover, if it is necessary to insert a plurality of implants, for applying a prosthesis B of a denture type, the surgeon no longer needs to worry, other than with the assemblies of the background art, about the mutual alignment among the various pins 2. The tabs 5 protrude to an extremely limited extent from the gum and therefore the risk that an incorrect alignment of the pins 2 and of the supporting elements 4 might cause an incorrect mutual positioning of the coupling points is reduced significantly.

Advantageously, both the pin 2 and the supporting element 4 can be provided with a plurality of shapes, as a function of the specific requirements of application for which the coupling assembly 1 according to the invention can be used.

For example, according to one possible embodiment, which is presented in FIG. 1 by way of non-limiting example of the application of the invention, the supporting element 4 is constituted by a hood 7 which has a substantially cylindrical shape and is open at one end face so as to form the above cited cavity 6. In order to produce a correct stable coupling, the internal wall or walls of the cavity 6 has a flared portion that is substantially complementary to the curvature of the outer lateral surface of the tab 5.

According to different embodiments, shown in FIGS. 2 to 5, the supporting element 4 is constituted by a ring 8, which in turn can be inserted in a substantially cylindrical sleeve 9, for the reference and support of additional prosthetic components (as will be described in more detail hereinafter).

Figure 3:
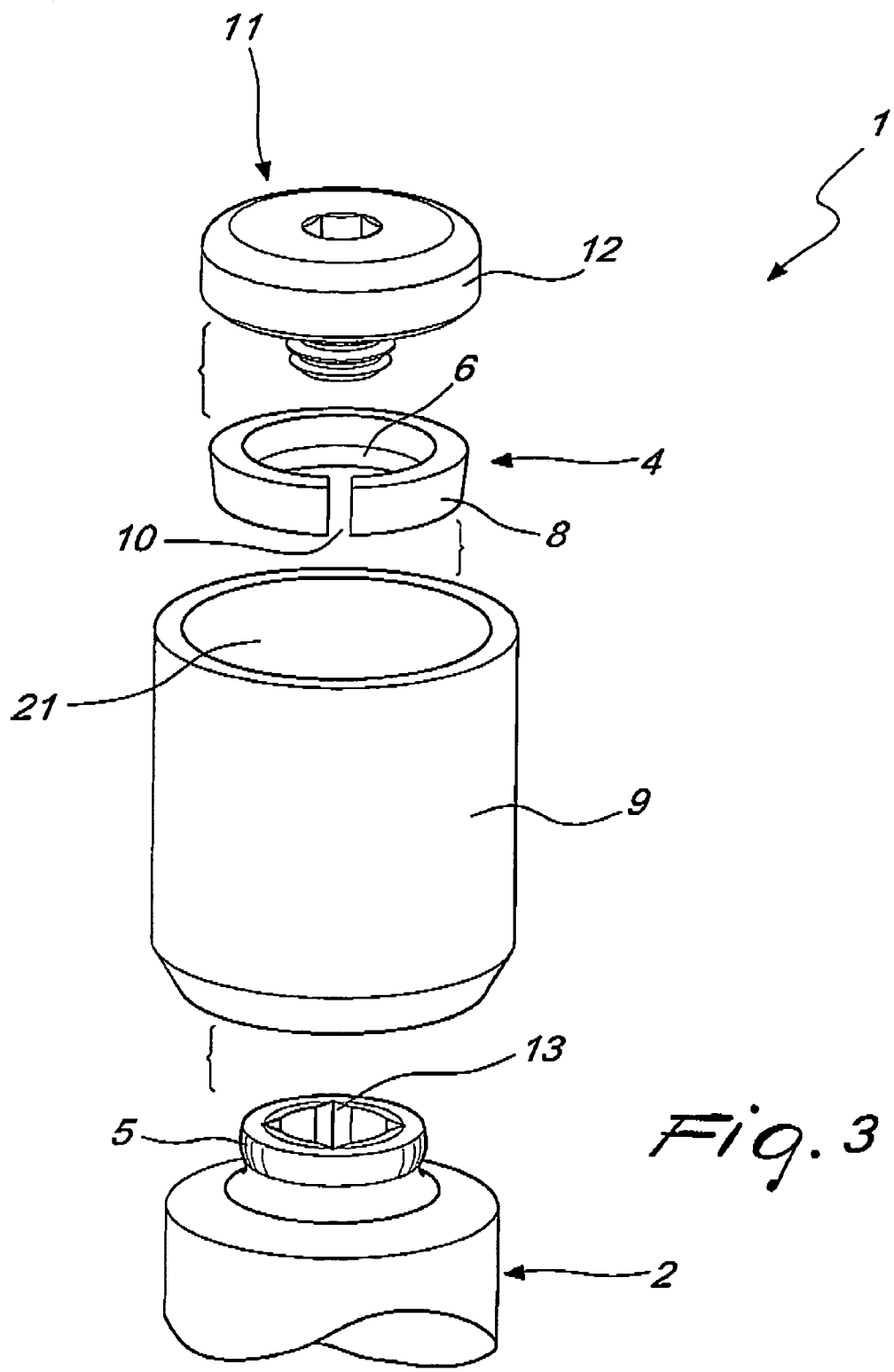
Figure 5:
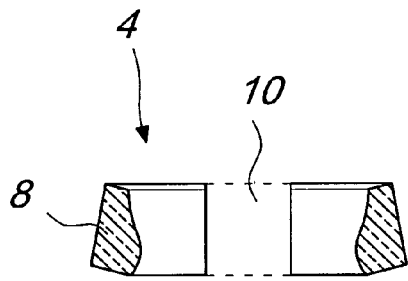
Figure 6:
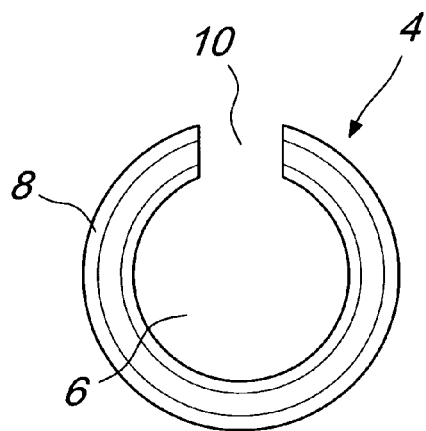

In order to increase its elastic deformability, the ring 8 can be provided with a notch 10, as in the embodiments shown in FIGS. 3, 5 and 6.

Conveniently, the coupling assembly 1 has fixing means 11 for fixing the supporting element 4 to the pin 2, which are capable of further contributing to the stability of their mutual coupling, making it fully rigid and non-removable.

More particularly, according to one possible embodiment, the fixing means 11 comprise a locking screw 12, which can be inserted coaxially in a corresponding female thread 13 formed within the tab 5.

Figure 4:
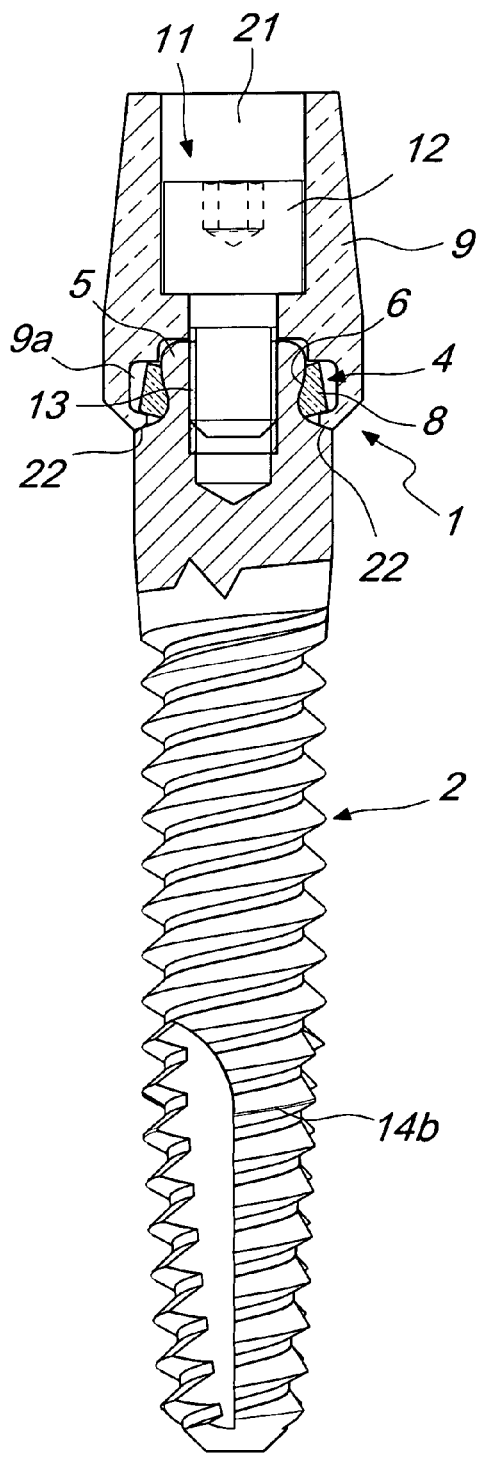
FIGS. 4 to 6 are views of the coupling assembly according to the invention in a third embodiment, and more particularly.

If one wishes in any case to maintain the possibility of removing the sleeve 9 at a later time in a practical and easy manner, it is possible to provide, as shown in FIG. 4, the internal surface of the sleeve 9 with a recess 9a formed at an end region thereof that is directed toward the pin 2.

As a consequence of a traction of the sleeve 9, after removal of the fixing means 11 the ring 8 (which can be made of a biocompatible polymeric material or of biocompatible titanium) can be deformed elastically, expanding within the recess 9a, allowing the convenient extraction of the sleeve 9 (whereas in the previously described solution, after removal of the fixing means 11 extraction is possible only by forcing and damaging irreparably the ring 8 and/or the sleeve 9).

Advantageously, for allowing rigid insertion in the bone portion A, the pin 2 has, on the side opposite the tab 5, a stem 14a, 14b, which is also threaded and is adapted for stable coupling to the bone portion A.

In greater detail, it is possible to provide on the stem 14a adapted threads to allow insertion (and subsequent coupling) in the seat formed in the preimplant 3 (as in FIG. 1).

As an alternative, as shown in FIG. 2, the stem 14b is self-tapping and can be inserted directly in the previously drilled bone (as in FIG. 2).

The possibility is moreover not excluded to provide stems 14a, 14b which are not threaded and can be inserted completely in a seat provided beforehand in the root of the tooth (the bone portion A) which has been conveniently reamed.

Moreover, the choice is provided to adopt coupling assemblies 1 in which the pin 2 can be coupled rigidly to an existing tooth (or in any case to a stable dental crown, even of a prosthetic type) and which are capable of producing a coupling with the supporting element 4 on the side of the latter.

According to this embodiment, the pin 2 is in fact constituted substantially by a tab 5 that protrudes from the sides of a tubular body conveniently keyed on the tooth.

It is then possible to stably couple the supporting element 4 to the pin 2, thus providing the stable shape on the side of the tooth.

This solution offers evident advantages with respect to the solutions typically used when it is necessary or preferable to install a prosthesis B on one or more teeth that are still stably anchored to the bone portion A.

According to known solutions, when faced with these needs one in fact resorts to a substantially spheroidal tab, which is connected by means of an adapted arm to the tubular body that is keyed on the tooth.

The choice to resort to the coupling assembly 1 (and therefore the lack of the arm) allows instead to contain the space occupied in the mouth of the patient and further makes it possible to reduce any flexural stresses to which the various components can be subjected (since they protrude from the tooth by a limited distance).

Moreover, if these components have to be provided by means of the known lost-wax technique, their reduced dimensions ensure the lack of shrinkage or porosities caused by imperfect cooling of the materials.

For facilitating the adaptation of the assembly 1 to parts which are known and/or of a commercial type, or to implants and/or prostheses B that have already been installed, but also more simply to allow easy coupling with the prosthesis B prepared by the laboratory, the supporting element 4 can be provided with a step 4a (or with other abutment means) to allow coupling to a matrix 15 provided on the prosthesis B; this further allows use of the assembly 1 according to the invention also for operations for maintenance and repair of existing prostheses B.

The coupling between the supporting element 4 and the matrix 15 allows, thanks to the deformability of the selected materials, slight oscillations of the prosthesis B with respect to the supporting element 4 (and with respect to the apparatus), thus compensating for any misalignments and small imperfections of the prosthesis B.

It should also be noted that the choice to resort to elastically deformable materials to provide the components described so far of the coupling assembly 1 allows a vertical yielding which compensates the effects of the masticatory load without bearing on the implants and the bone portion A.

With particular reference to the ring 8 (and to the embodiment of FIGS. 2 and 3), making it of deformable material and optionally oversizing it during design with respect to the requirements of simple coupling allows the ring 8 to apply a counterpressure on the locking screw 12, in practice behaving like a locking nut, thus contributing to the stability of the coupling.

To further reduce the risk of bearing on the implants and on the bone portion A, it is possible to shape the pin 2 and the supporting element 4 so as to maintain an empty space between the base of the latter and the edge of the gum; this space is occupied by the supporting element 4 and thus compensates for any elastic yielding produced by the masticatory load.

The solutions described above can be used for various types of implant, both for traditional ones and for those known as immediate load implants; it is further possible to use coupling assemblies 1 according to what is described to provide mini-implants (again both the traditional type and the immediate load type).

The use of the coupling assembly 1 to apply mini-implants makes it possible to perform surgical procedures which are simple and much quicker than those that provide for resorting to traditional implants.

In any case, use of the assembly 1 for the insertion of traditional implants is still possible, and therefore provides for at least one first session, in which the surgeon works with a scalpel to open the bone portion A constituted by the gum and to access the underlying bone. By means of an appropriate milling machine, he/she can then form a channel into which the preimplant 3 required to accommodate the stem 14a is to be inserted (if, of course, the preimplant 3 is not already present because it originates from a previous operation). Then he/she can reposition the flaps of the gum and close the wound with stitches (according to a surgical technique of the known type).

After a period that can vary between three and six months it is possible to access the preimplant 3 again to insert the pin 2 and then the supporting element 4 and continue in the activities required for the insertion of the prosthesis B.

The method according to the invention for the installation of a dental prosthesis B on a plurality of coupling assemblies 1 consists first of all in coupling rigidly a plurality of pins 2 to a bone portion A (or the like).

At this point the method according to the invention provides, in a step b., for the keying of a substantially cylindrical stub 16 onto each pin 2 in order to allow the reference and support of additional prosthetic components.

Once the stubs 16 have been keyed, it is possible, in a step c., to obtain a substantially mirror-symmetrical impression or imprint (typically made of elastomer) of the bone portion A and of the stubs 16, in order to provide the prosthesis B: during this step c., the stubs 16 are driven into the impression or imprint so as to constitute a reference for subsequent correct sizing of the prosthesis B.

Figure 7:
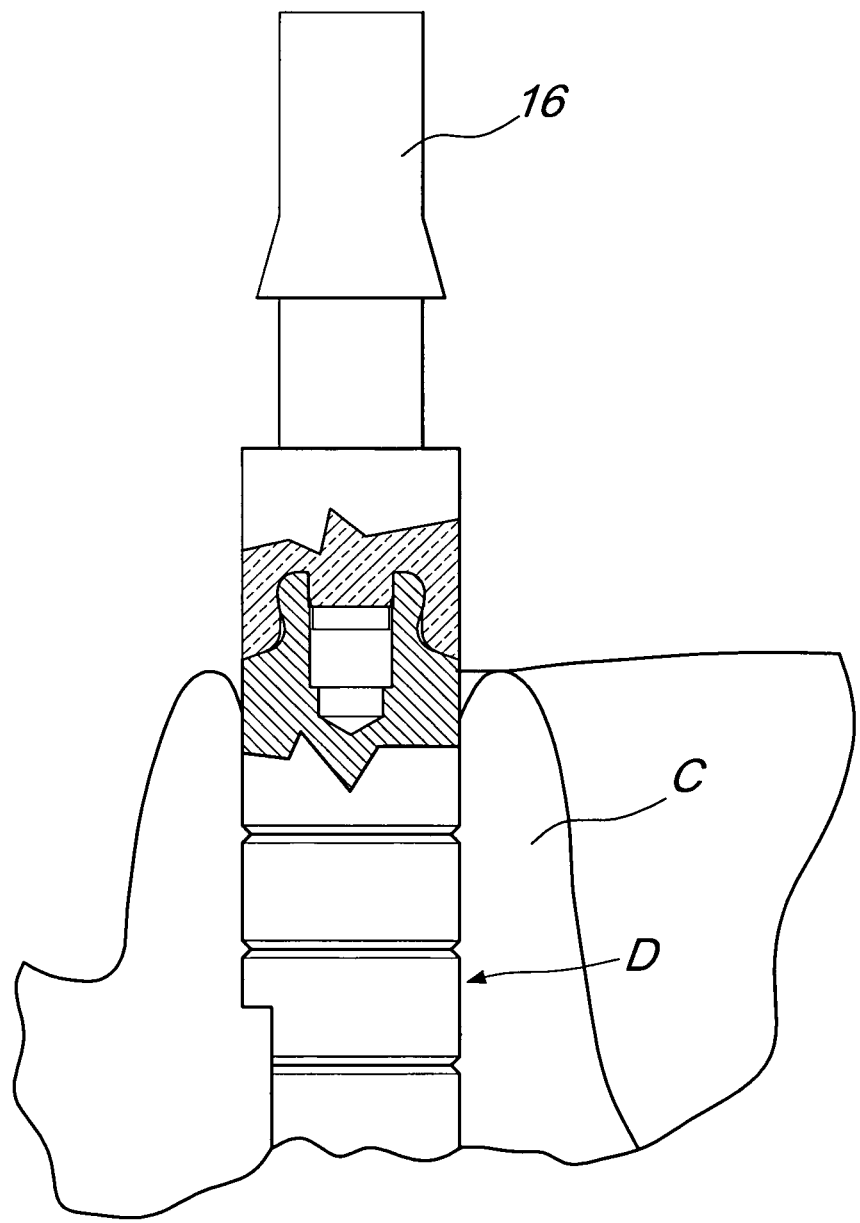
FIGS. 7 and 8 are views of further uses of the coupling assembly according to the invention, adapted for the execution of further work.

Once these first operations, which can be performed by a dentist in the first session with the patient, have ended, a dental laboratory, which receives the imprint, models, in a step d., a cast C (typically made of plaster) of the bone portion A, and it is possible to arrange inserts D (which simulate the pins 2) on the cast C to replicate the shape assumed by the assemblies 1 associated with the bone portion A (as in the example of FIG. 7).

With an optimum replica of the bone portion A, constituted by the cast C, at one's disposal, it is possible in a step e., in the dental laboratory, to provide, on the basis of the cast C, a bar 17 (according to known methods, such as for example the lost-wax casting method, which makes it possible to obtain a prosthesis B that is very strong by resorting to prefabricated components which can be calcined).

The bar 17 can be arranged transversely to the edge of the bone portion A, thanks to sleeves 9 which are provided appropriately and are fixed to the bar 17 and can be coupled to the pins 2: the bar 17 (with the sleeves 9 fixed thereto) thus constitutes a base for coupling to a respective seat 18 that is formed in the prosthesis B.

The laboratory can then, in a step f., on the basis of the cast C also build the prosthesis B to be coupled to the bar 17 cited above.

Figure 8:
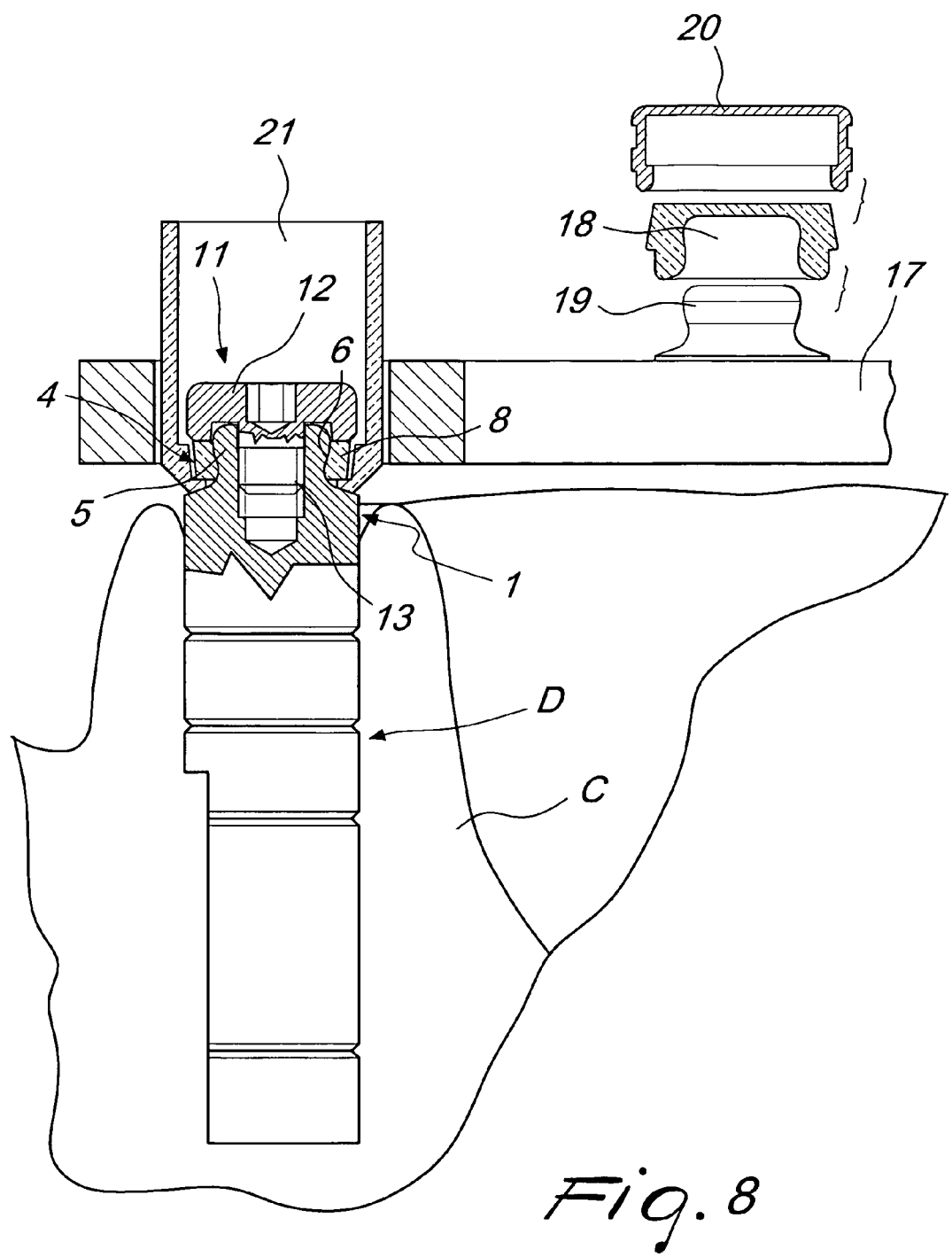

For example, as can be seen in FIG. 8, the coupling between the bar 17 and the prosthesis B can be provided by replicating substantially the methods already described for the assembly 1: the possibility is thus provided to form, along the bar 17, protrusions 19 that are shaped like the tab 5 and are adapted to be accommodated in the seat 18, which in turn can be accommodated in a block 20 that is jointly connected to the prosthesis B.

These protrusions 19 can be arranged above the bar 17, along an axis that is substantially perpendicular thereto and to the edges of the gum (as in FIG. 8), or protrude from the sides of the bar 17 (for a coupling direction that is parallel to the edges of the gum), as a function of the specific application requirements.

After completing the step f., in a second session the dentist can proceed with the final steps of the installation of the prosthesis B: he/she can in fact, in a step g., arrange the bar 17 transversely to the edge of the gum, coupling it to the pins 2 by means of the sleeves 9.

Subsequently, in a step h., the dentist can accommodate by elastic forcing the supporting elements 4 on the tab 5 of each pin 2, thus providing a configuration for stable coupling between the pins 2 and the supporting elements 4 and between the supporting elements 4 and the sleeves 9.

More precisely, in step h. the dentist associates the sleeves 9 (which are fixed to the bar 17) with the pins 2, in order to then associate a ring 8 with each pin 2.

In order to increase the stability of the coupling and prevent subsequent removals thereof, it is optionally possible to resort to the fixing means 11 (as already shown) to lock each supporting element 4 on the pins 2.

Conveniently, according to the embodiment presented in the figure, which is a non-limiting example of the application of the invention, the sleeve 9 has a tubular shape and the duct 21 formed inside the sleeve 9 has, at one end of the sleeve 9, a shoulder 22 that is adapted to abut against the base of the ring 8, so as to ensure mutual coupling (reinforced by the presence of the fixing means 11).

Finally, in a step i. it is possible to install detachably the prosthesis B in the mouth of the patient, associating it with the bar 17.

According to the described method, the prosthesis B therefore does not mate with a plurality of pins 2 or other components but only with the bar 17, thus ensuring greater stability and reduced discomfort caused by small misalignments of the individual components (which are compensated by the bar 17).

More precisely, the presence of the bar 17, which is interposed between the pins 2 and the prosthesis B, makes it possible to compensate for any lack of parallelism between the pins 2, which according to known methods could cause coupling with the prosthesis B to be problematic.

By resorting to the bar 17, provided on the basis of the position and orientation of the various pins 2 (as described), optimum coupling with such pins is ensured, while it is practical and convenient to couple in turn the bar 17 to the prosthesis B.

The coupling between the supporting elements 4 and the pins 2, as well as the coupling between the supporting elements 4 and the bar 17, can be rendered permanent by way of the fixing means 11 and optional additional steps for welding or mutual bonding of the parts.

It should be noted, however, that the choice to resort to fixing means 11 such as the screw 12, on the one hand, as mentioned, ensures that the coupling persists over time, and on the other hand allows its removal by the dentist in ways that preserve the other elements installed in the mouth.

It is in fact sufficient to operate on the screw 12, by unscrewing it, and then extract the ring 8 (or optionally destroy it) to allow access to the pin 2 or other internal elements, in order to allow them to be cleaned and inspected, without thereby compromising the remaining, work. Once inspection has ended, it is therefore simple to restore the coupling by reassociating the ring 8 (optionally a new ring 8) with the pin 2 to then provide a new fixation by means of the screw 12.

The method according to the invention makes it possible to achieve installation of the prosthesis B a few days after fixing the pins 2 to the bone portion A and therefore a few days after starting with said method.

In particular, as already noted, steps a. to c. can be performed by the dentist in a first session; subsequently, a dental laboratory can perform in a few days steps d. to f., to then return to the dentist the bar 17 (with the sleeves 9) and the prosthesis B, by means of which the dentist, in a second session, completes the method according to the invention (performing steps g. to i.).

In any case, the low cost of the components used and the possibility mentioned earlier to complete the entire method according to the invention in a few days positively allow keeping the operation costs low, with evident benefits for the patient, without thereby affecting the economic margin of the surgeon and of the dental technician.

Conveniently, at the end of step c., the method according to the invention can entail the protection, in a step j., of the bone portion A and the assemblies 1 by means of a temporary plate.

Such temporary plate can be applied to the gum for protecting the bone portion A and the components of the coupling assembly 1 that are already associated therewith, while the dental laboratory is in the process of completing steps d. and e.

Further, by spreading the part of the plate designed to contact the gum with appropriate disinfectant substances it is possible to avoid the risk of causing discomfort to the patient.

The kit for the application of prostheses B comprises at least one plurality of pins 2, a plurality of respective supporting elements 4 and a set of additional accessories and tools (for example made of materials which can be calcined and/or titanium) for performing the installation method described in the previous paragraphs.

Each pin 2 can be coupled stably with a respective supporting element 4 by accommodation, by elastic forcing, of the tab 5 of each pin 2 in respective cavities 6 formed in the corresponding supporting elements 4.

More particularly, the set of additional accessories and tools comprises at least one bar 17 (made of material which can be calcined) and a plurality of sleeves 9, pins 16 and inserts D.

In the kit 24 the dentist can thus find all the components needed for the insertion of one or more implants for subsequent coupling with one or more prosthetic teeth.

More generally, the possibility is provided to equip the kit with all the components needed to provide and insert any type of prosthesis B and to perform the method described above: in the kit, the surgeon in fact finds the pins 2, the supporting elements 4 and the accessories (such as for example the stubs 16) needed to take the imprint in order to provide the cast C and subsequently the prosthesis B.

In conclusion, regardless of the type of implant and prosthesis B with which the patient is to be provided, the kit comprises all the necessary components, thus providing the dentist with a single reference standard that accompanies him/her in the various steps of the operation (and in subsequent operations).

This avoids the necessity of having to contact several suppliers and use different types of components (which are often mutually incompatible), thus ensuring a reduction in the times and costs linked to the operations and higher effectiveness and likelihood of positive outcomes thereof.

The terms "substantial" and "substantially", when referred to shapes or dimensions of elements disclosed herein, will be interpreted as meaning that those shapes or dimensions to which they refer have the mentioned configuration or dimensions but for tolerances that are known by those skilled in the art, to be usual for the technical field involved.

In practice it has been found that the coupling assembly according to the invention fully achieves the intended aim, since the choice to resort to a tab that is shaped like a substantially equatorial portion of a sphere for the pin that is coupled to the bone portion, a tab whose outer lateral surface can abut against the inner side walls of the abutment element that can be associated with the prosthesis, produces a stable coupling configuration, at the same time containing the space occupation within the mouth, thus sparing the patient any annoying inconveniences.

The invention thus conceived is susceptible of numerous modifications and variations, all of which are within the scope of the appended claims; further, all the details may be replaced with other technically equivalent elements.

In the exemplary embodiments shown, individual characteristics, given in relation to specific examples, may actually be interchanged with other different characteristics that exist in other exemplary embodiments.

Moreover, it is noted that anything found to be already known during the patenting process is understood not to be claimed and to be the subject of a disclaimer.

In practice, the materials used, as well as the dimensions, may be any according to requirements and to the state of the art.

The disclosures in Italian Patent Application No. BO2009A000279 from which this application claims priority are incorporated herein by reference.

What is claimed is:

1. A coupling assembly for dental implants, comprising:
at least one pin, which is rigidly coupleable to a bone portion of a patient;
a supporting element that has a cavity formed therein which has an internal wall; and
a substantially cylindrical sleeve,
wherein said supporting element is constituted by a ring that is positioned on the pin, and said substantially cylindrical sleeve has an inside duct, said inside duct having an inwardly extending bottom shoulder that is secured between said ring and a surface of the pin for providing reference and support for additional prosthetic components, and said inside duct extending from said bottom shoulder to a top edge thereof in a direction away from said pin in an assembled configuration of the coupling assembly,
and wherein said pin has at a first end portion thereof that lies opposite a second one designed for connection to the bone portion, a protruding tab, that is accommodatable by elastic forcing in said cavity formed in said ring for stable coupling between said pin and said supporting element,
and wherein said tab has a shape of a disc with an outer lateral surface that is constituted by a fragment of a spherical surface which comprises a great circle of a sphere and forms a curvature with a portion that tapers towards said pin, said internal wall of said cavity of the ring having a flared portion that is complementary to said tapering portion of the curvature of the outer lateral surface of said tab, said outer lateral surface being adapted to abut, with at least a part of said tapering thereof, against said internal wall of said cavity, so as to determine the stable coupling configuration,
the coupling assembly further comprising a locking screw that is screwable into a female thread formed in said tab, and
wherein in said assembled configuration of the coupling assembly said bottom shoulder of said sleeve is locked between said surface of said pin and said ring, and said ring is locked between said bottom shoulder of said sleeve and said locking screw that is screwed into said female thread formed in said tab.

2. The coupling assembly of claim 1, wherein said pin has, at said second end thereof, opposite said tab, a stem which is threaded and is suitable for stable coupling to the bone portion.

3. The coupling assembly of claim 1, wherein said ring is made of an elastically deformable material.

4. The coupling assembly of claim 1, wherein said ring is provided with a notch suitable to increase elastic deformability of the ring.

5. The coupling assembly of claim 1, wherein in said assembled configuration said locking screw is arranged inside said inside duct of said sleeve.

6. A coupling assembly for dental implants, comprising:
at least one pin, which is rigidly coupleable to a bone portion of a patient;
a supporting element that has a cavity formed therein which has an internal wall;
fixing means for fixing said supporting element to said pin, and
a substantially cylindrical sleeve,
wherein said supporting element is constituted by a ring that is positioned on the pin and said substantially cylindrical sleeve has an inside duct, said inside duct having an inwardly extending bottom shoulder that is secured between said ring and a surface of the pin for providing reference and support for additional prosthetic components, and said inside duct extending from said bottom shoulder to a top edge thereof in a direction away from said pin in an assembled configuration of the coupling assembly,
and wherein said pin has at a first end portion thereof that lies opposite a second one designed for connection to the bone portion, a protruding tab, that is accommodatable by elastic forcing in said cavity formed in said ring for stable coupling between said pin and said supporting element,
and wherein said tab has a shape of a disc with an outer lateral surface that is constituted by a fragment of a spherical surface which comprises a great circle of a sphere and forms a curvature with a portion that tapers towards said pin, said internal wall of said cavity of the ring having a flared portion that is complementary to said tapering portion of the curvature of the outer lateral surface of said tab, said outer lateral surface being adapted to abut, with at least a part of said tapering thereof, against said internal wall of said cavity, so as to determine the stable coupling configuration,
and wherein said fixing means comprises a locking screw that is insertable coaxially in a corresponding female thread formed within said tab so as to allow said ring to apply a counterpressure on said locking screw, wherein in said assembled configuration of the coupling assembly said bottom shoulder of said sleeve is locked between said surface of said pin and said ring, and said ring is locked between said bottom shoulder of said sleeve and said locking screw that is screwed into said female thread formed in said tab.

7. The coupling of claim 6, wherein said ring is provided with a notch suitable to increase elastic deformability of the ring.

8. The coupling of claim 6, wherein said cylindrical sleeve has a tubular shape with said duct formed inside, said duct being provided at one end thereof with said bottom shoulder that is adapted to abut against a base of said ring, so as to ensure mutual coupling of the ring and cylindrical sleeve.

9. The coupling assembly of claim 6, wherein said ring is made of an elastically deformable material.

10. The coupling assembl y of claim 6, wherein in said assembled configuration said locking screw is arranged inside said inside duct of said sleeve.

11. A coupling assembly for dental implants, comprising:
at least one pin, which is rigidly coupleable to a bone portion of a patient;
a supporting element that has a cavity formed therein which has an internal wall; and
a substantially cylindrical sleeve;
wherein said supporting element is constituted by a ring that is positioned on the pin, said cylindrical sleeve having an inside duct and a recess that is provided on an internal surface of said cylindrical sleeve at an end region thereof that is directed toward the pin and so as to face said ring upon keying of said cylindrical sleeve on said ring, said inside duct having an inwardly extending bottom shoulder that is secured between said ring and a surface of the pin for providing reference and support for additional prosthetic components; and
said inside duct extending from said bottom shoulder to a top edge thereof in a direction away from said pin in an assembled configuration of the coupling assembly,
and wherein said pin has at a first end portion thereof that lies opposite a second one designed for connection to the bone portion, a protruding tab, that is accommodatable by elastic forcing in said cavity formed in said ring for stable coupling between said pin and said supporting element;
and wherein said tab has a shape of a disc with an outer lateral surface that is constituted by a fragment of a spherical surface which comprises a great circle of a sphere and forms a curvature with a portion that tapers towards said pin, said internal wall of said cavity of the ring having a flared portion that is complementary to said tapering portion of the curvature of the outer lateral surface of said tab, said outer lateral surface being adapted to abut, with at least a part of said tapering thereof, against said internal wall of said cavity, so as to determine the stable coupling configuration,
the coupling assembly further comprising a locking screw that is screwable into a female thread formed in said tab,
wherein in said assembled configuration of the coupling assembly said bottom shoulder of said sleeve is locked between said surface of said pin and said ring, and said ring is locked between said bottom shoulder of said sleeve and said locking screw that is screwed into said female thread formed in said tab.

12. The coupling assembly of claim 11, wherein said ring is made of an elastically deformable material.

13. The coupling assembly of claim 11, wherein said ring is provided with a notch suitable to increase elastic deformability of the ring.

14. The coupling assembly of claim 11, wherein in said assembled configuration said locking screw is arranged inside said inside duct of said sleeve.

\* \* \* \* \*